(12) United States Patent
Baxi

(10) Patent No.: US 9,204,814 B2
(45) Date of Patent: Dec. 8, 2015

(54) HAND-HELD HEART MONITOR

(71) Applicant: Intel Corporation, Santa Clara, CA (US)

(72) Inventor: Amit Baxi, Thane (IN)

(73) Assignee: Intel Corporation, Santa Clara, CA (US)

( * ) Notice: Subject to any disclaimer, the term of this patent is extended or adjusted under 35 U.S.C. 154(b) by 462 days.

(21) Appl. No.: 13/655,966

(22) Filed: Oct. 19, 2012

(65) Prior Publication Data

US 2014/0114166 A1 Apr. 24, 2014

(51) Int. Cl.
*A61B 5/0404* (2006.01)
*A61B 5/0408* (2006.01)
*A61B 5/00* (2006.01)

(52) U.S. Cl.
CPC ............ *A61B 5/0404* (2013.01); *A61B 5/0408* (2013.01); *A61B 5/04085* (2013.01); *A61B 5/6898* (2013.01)

(58) Field of Classification Search
CPC .......................... A61B 5/0404; A61B 5/04085
USPC .................................................. 600/393, 509
See application file for complete search history.

(56) References Cited

U.S. PATENT DOCUMENTS

| 4,535,783 | A * | 8/1985 | Marangoni | 600/524 |
| 7,647,093 | B2 * | 1/2010 | Bojovic et al. | 600/509 |
| 8,332,019 | B2 * | 12/2012 | Shimuta et al. | 600/509 |
| 8,412,313 | B2 * | 4/2013 | Amitai et al. | 600/509 |
| 8,644,915 | B2 * | 2/2014 | Chou | 600/509 |
| 8,903,477 | B2 * | 12/2014 | Berkner | 600/509 |
| 2006/0047210 | A1 * | 3/2006 | Moroki et al. | 600/509 |
| 2009/0182205 | A1 * | 7/2009 | Cho et al. | 600/301 |

* cited by examiner

*Primary Examiner* — Lee S Cohen
(74) *Attorney, Agent, or Firm* — International IP Law Group, PLLC

(57) ABSTRACT

A heart monitor is provided herein. The heart monitor includes a housing and first and second electrodes disposed in a first surface of the housing. At least a third electrode is disposed on a second surface of the housing. The first and second electrodes are held by a user with his left and right hand respectively, while the third electrode contacts the user's torso or left leg. A processor records lead measurements corresponding to voltage differences between the first, second and third electrodes.

5 Claims, 10 Drawing Sheets

600

600

700

700

800

800

900

900

# HAND-HELD HEART MONITOR

TECHNICAL FIELD

The present invention relates to hand-held heart monitors and methods of using hand-held heart monitors.

BACKGROUND ART

In clinical electrocardiogram (ECG) machines that record multiple ECG leads, ECG electrodes are connected to an ECG device using electrical cables and electrodes. Multiple ECG leads enable a physician to "view" the heart from different directions to diagnose a heart condition. However, this method of recording requires accessories like disposable electrodes and ECG cables and it is difficult to set up and remove.

New generation Personal ECG monitors (PEMs) try to solve this usability problem to some extent using two metal electrodes disposed on the device itself. To record ECG, a patient has to either hold the device in his hand or touch it to his chest, so that the metal electrodes touch his body, picking up a single ECG lead.

PEMs with embedded electrodes offer convenience but are severely limited in diagnostic capability since they usually do not measure more than one ECG lead. A single ECG lead is not sufficient to detect heart conditions like ischemia and infarction because in standard clinical practice, doctors are trained to diagnose a heart condition by analyzing 12 ECG leads, which gives them a "view" of a heart's electrical activity from different directions. As a result, though conventional PEMs with embedded electrodes offer simplicity, they lack clinical diagnostic efficacy because they cannot measure all 12 ECG leads.

BRIEF DESCRIPTION OF THE DRAWINGS

The same numbers are used throughout the disclosure and the figures to reference like components and features. Numbers in the 100 series refer to features originally found in FIG. 1; numbers in the 200 series refer to features originally found in FIG. 2; and so on.

DESCRIPTION OF THE EMBODIMENTS

A heart monitor may employ electrodes disposed on the surface of the heart monitor to provide a recording of the electrical activity of the heart, known as an electrocardiogram (ECG), without using adhesive electrodes connected to a chest and wires connecting the electrodes to a device. The number of electrodes disposed on the surface of the heart monitor will determine the number of ECG leads that can be measured by the heart monitor. For example, three electrodes may allow at least nine ECG leads to be measured. In another example, four electrodes may allow twelve ECG leads to be measured. In embodiments, at least one of the electrodes is configured to contact a user's hand while the user holds the heart monitor against the user's torso. In this way, measurements at several electrode positions can be taken simultaneously.

Figure 1:
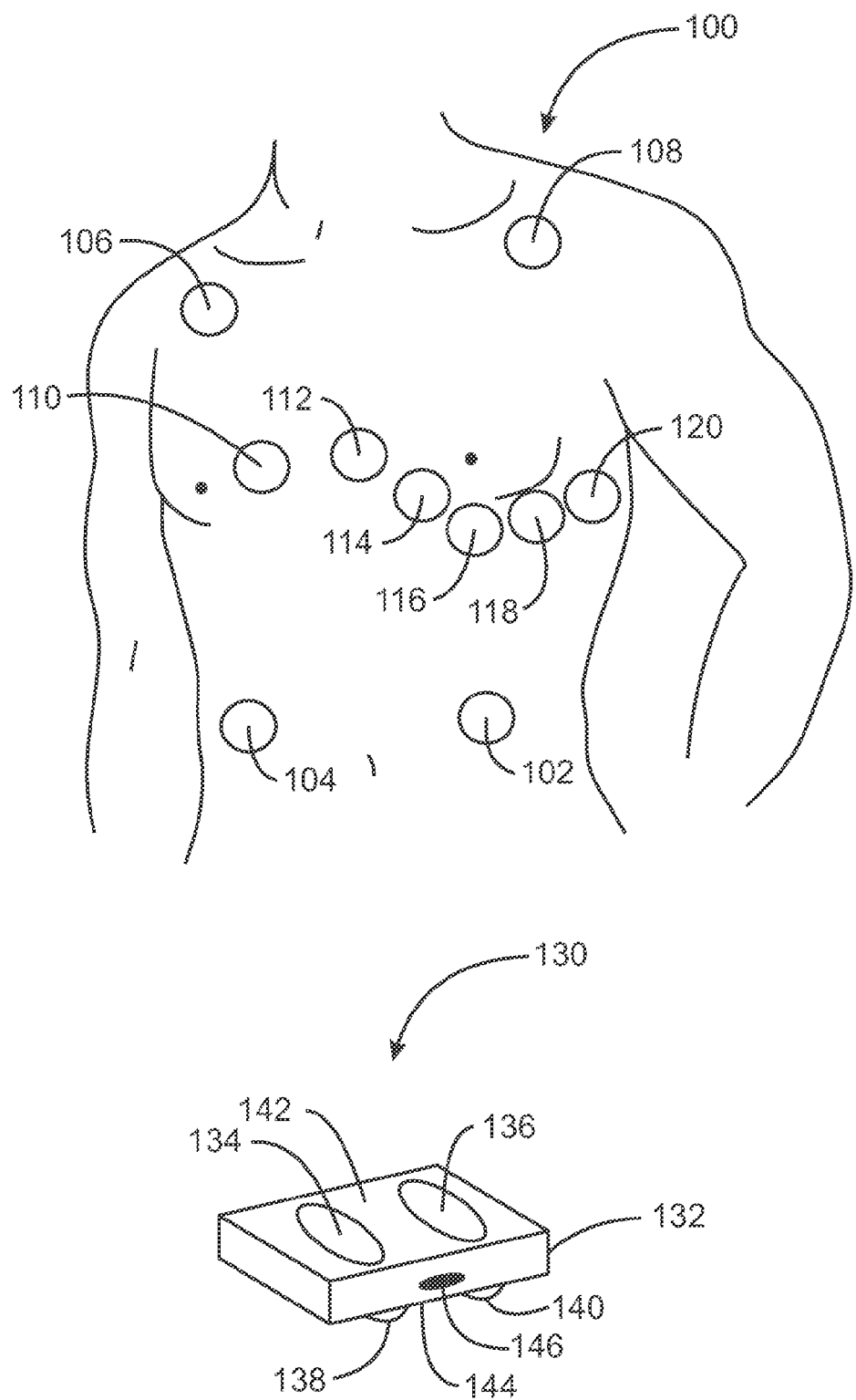
FIG. 1 is an illustration of electrode positions for a 12-lead ECG and a heart monitor to contact the electrode positions in accordance with an embodiment.

FIG. 1 is an illustration of electrode positions for a 12-lead ECG and an illustration of a heart monitor to contact the electrode positions in accordance with an embodiment. As used herein, the term "lead" refers to the voltage difference between two electrode positions. Various leads may be measured by placing electrodes at the electrode positions shown in FIG. 1. For example, twelve leads may be measured using the electrode positions shown in FIG. 1. The electrode positions are limb electrode positions left leg (LL) 102, right leg (RL) 104, right arm (RA) 106, and left arm (LA) 108, and chest electrode positions V1 110, V2 112, V3 114, V4 116, V5 118, and V6 120. Furthermore, three augmented ECG leads, aVR, aVL, and aVR, may be derived from measurements taken at limb electrode positions RA 106, LA 108, and LL 102. Augmented ECG lead aVR may be derived using the equation aVR=RA−½(LA+LL). Augmented ECG lead aVL may be derived using the equation $$aVL = LA - \frac{1}{2}(RA + LL).$$

Augmented ECG lead aVF may be derived using the equation $$aVF = LL - \frac{1}{2}(RA + LA).$$

Measurements taken at each of the electrode positions may also be used to derive modified chest leads, which appear similar in waveform shape and morphology to conventional chest leads. Modified chest leads measure differential signals between each chest electrode position and the left arm electrode position. Modified Chest Lead 1 (MCL1) measures the difference between electrode positions V1 110 and LA 108, Modified Chest Lead 2 (MCL2) measures the difference between electrode positions V2 112 and LA 108, Modified Chest Lead 3 (MCL3) measures the difference between electrode positions V3 114 and LA 108, Modified Chest Lead 4 (MCL4) measures the difference between electrode positions V4 116 and LA 108, Modified Chest Lead 5 (MCL5) measures the difference between electrode positions V5 118 and LA 108, and Modified Chest Lead 6 (MCL6) measures the difference between electrode positions V6 120 and LA 108.

A hand-held heart monitor 130 may include a housing 132 and four electrodes 134, 136, 138, and 140. Although four electrodes are shown, it will be appreciated that other numbers of electrodes may be included in the monitor 130, for example, three electrodes, five electrodes, or more. In an example, two electrodes 134 and 136 may be disposed on a first surface 142 of the housing such that the user can easily contact electrodes 134 and 136 with the user's hand during the testing process. Two additional electrodes 138 and 140 may be disposed on a second surface 144 of the housing 132 to be placed against the user's torso during the testing process. In this way, four electrode positions can be accessed simultaneously. The heart monitor 130 may further include a processor to record electrocardiogram (ECG) lead measurements.

A button 146 may be disposed on the surface of housing 132 at a position that is conveniently accessible by the user during the testing process without the user repositioning his hands between each test step, as illustrated in FIG. 1. In an example, pushing the button 146 may activate the heart monitor. In another example, pushing the button 146 may indicate to the heart monitor to move to a next measurement step. The button 146 may be pressed by the user after each measurement step to indicate to the heart monitor to move to the next step. In another example, the heart monitor is activated using commands transmitted remotely over a wireless communications interface, in which case, button 146 may be eliminated.

Figure 2:
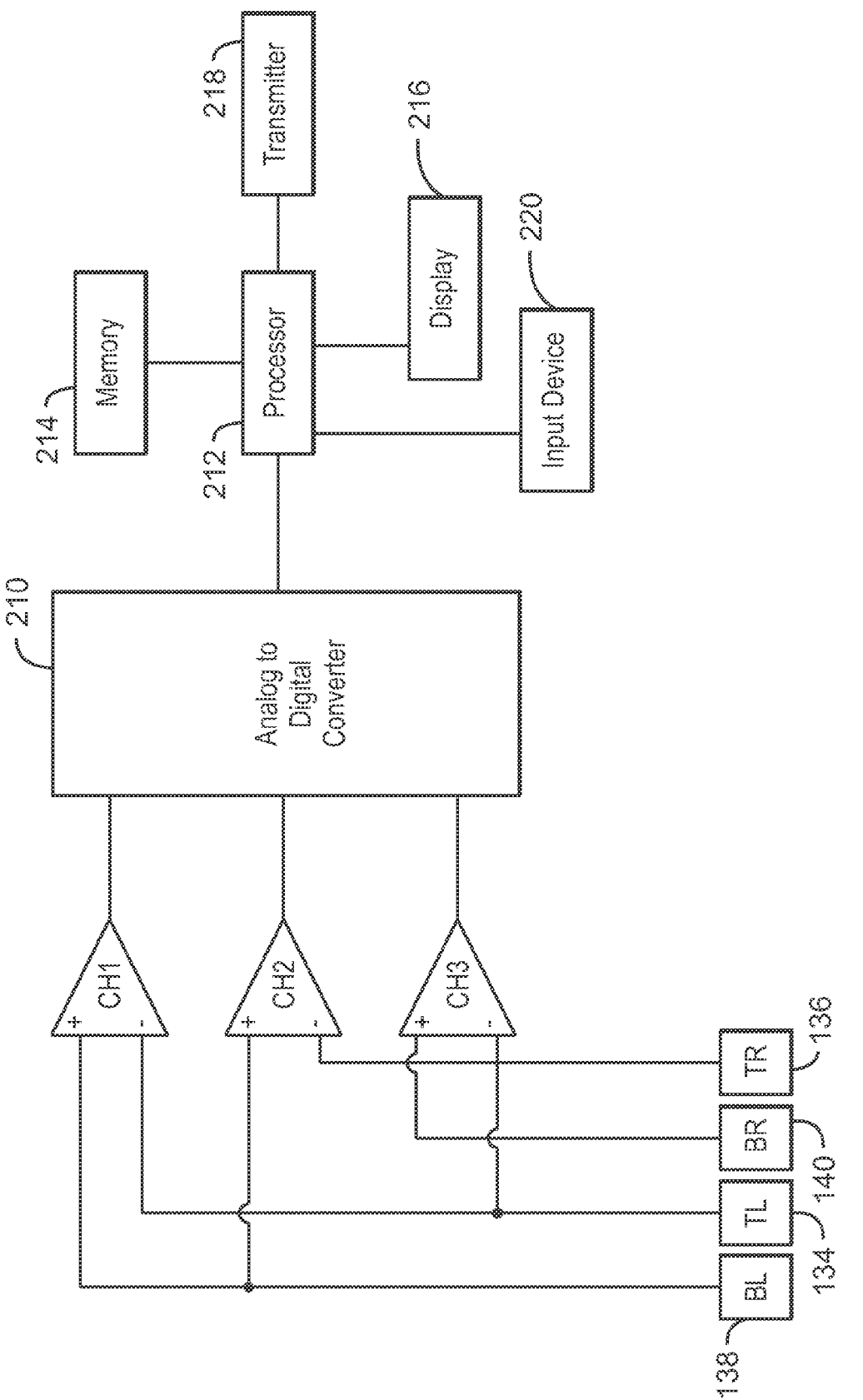
FIG. 2 is an illustration of internal circuitry in accordance with an embodiment.

FIG. 2 is an illustration of internal circuitry in accordance with embodiments. The electrodes 134, 136, 138, and 140 may be electrically connected to an internal circuitry 200 within the heart monitor. In an example, the internal circuitry 200 may include at least three parallel ECG amplifier channels, such as amplifier channels CH1, CH2, and CH3. The amplifier channels CH1, CH2, and CH3 may be connected to inputs of an analog to digital converter (ADC) 210. Each amplifier channel CH1, CH2, and CH3 may be electrically hard wired to at least one of the electrodes 134, 136, 138, and 140. For example, CH1 may be electrically hard wired to an electrode 134 on the top surface of the heart monitor and an electrode 138 on the bottom surface of the heart monitor 130.

The analog to digital converter 210 may be connected to a processor 212. The processor 212 may be connected to a memory 214. The memory 214 may be an internal memory, such as a memory to store measured ECG data. In an example, the memory 214 may be a flash memory.

The processor 212 may also be connected to a display 216. The display 216 may be provided on the surface of the heart monitor. The display 216 may visually provide information to a user, such as a patient or health care provider. For example, the display 216 may provide measured ECG data to a user. The display 216 may be any suitable type of display material. In an example, the display 216 may be a liquid crystal display (LCD) screen. In another example, the display 216 may be a light emitting diode (LED) screen.

The processor 212 may be connected to a transmitter 218. The transmitter 218 may transmit data, such as measured ECG data, to another location. The other location may be another device. In an example, the device may be a back-end server, such as a heath care provider's server. In another example, the device may be a memory device or a mobile phone. The hand-held monitor may transmit the data through a variety of methods. For example, the hand-held heart monitor may transmit the data over an internet connection, such as a wired internet connection, a LAN connection, or a WAN internet connection. In another example, the data may be transmitted over a telephone connection, such as a landline telephone connection or a wireless telephone connection. In another example, data may be transmitted by the heart monitor using wireless communication technology such as Bluetooth, Zigbee, or WiFi to another device such as a mobile phone or a computing device such as a tablet PC or laptop. In a further example, the data may be transmitted over a fax line.

The processor 212 may also be connected to at least one input device 220. Input devices 220 may allow a user to input data to the hand-held heart monitor. For example, the user may input information about his or herself, such as his or her physical condition. In another example, the user may input operating instructions to the hand-held heart monitor. Input devices 220 may be any device allowing the user to communicate with the heart monitor, such as a keyboard or a mouse. The input device 220 may also be at least one button.

It will be appreciated that the circuit shown in FIG. 2 is only one example of a circuit that could be used in accordance with embodiments and that various other circuits may be used depending on the design considerations of a particular implementation. For example, the internal circuitry 230 may include fewer that three ECG amplifier channels, such as amplifier channels CH1 and CH2. Furthermore, a switching circuit or multiplexer may be used to connect the electrodes 134, 136, 138, and 140 to the inputs of an ECG amplifier channels based on the logic level on a SELECT pin of the multiplexer. In an example, the multiplexer may be a 2:1 analog multiplexer. The multiplexer may electrically connect the electrodes 134, 136, 138, and 140 in different combinations to the inputs of an ECG amplifier, for example ECG amplifier CH2.

Figure 3A:
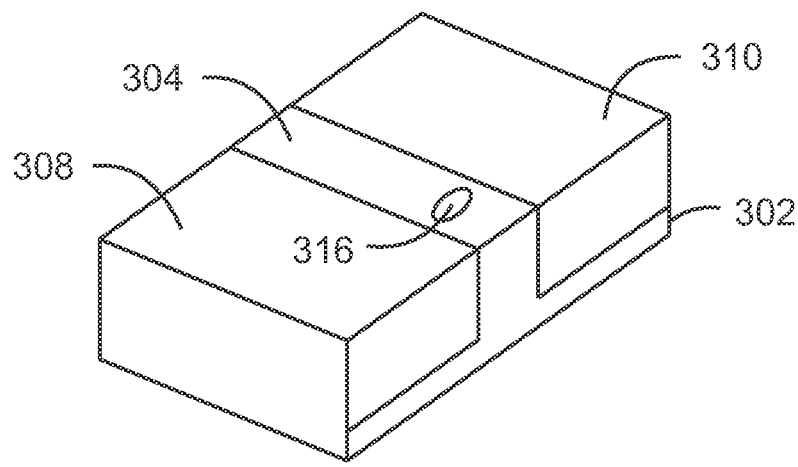
FIG. 3a is an illustration of a top perspective view of a heart monitor in accordance with an embodiment.
Figure 3B:
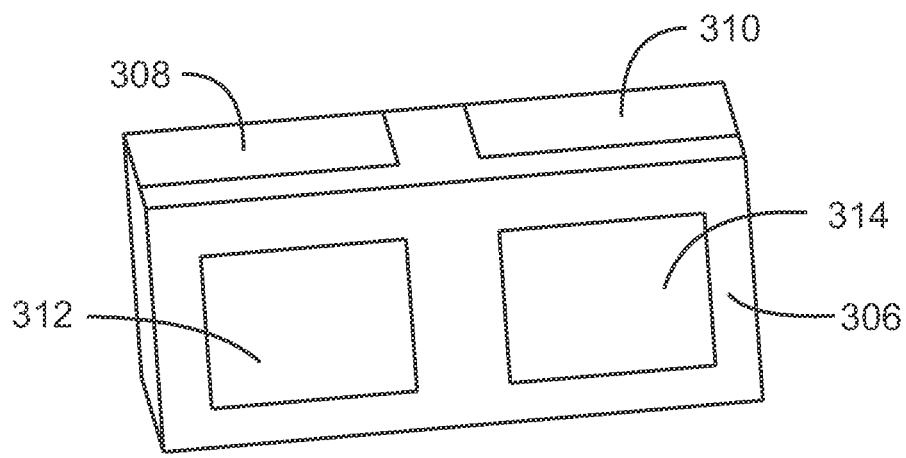
FIG. 3b is an illustration of a bottom perspective view of a heart monitor in accordance with an embodiment.

FIGS. 3a-3b are illustrations of perspective views of a heart monitor 300 in accordance with an embodiment. Disposed on a first surface 304 of a housing 302 are first 308 and second 310 electrodes and disposed on a second surface 306 of the housing 302 are third 312 and fourth 314 electrodes. In an example, the electrodes may be disposed on at least one surface of housing 302. In an example, the first surface 304 and the second surface 306 may be directly opposite and parallel to each other. In an example, the first surface 304 may be the top surface of the heart monitor. In another example, the second surface 306 may be the bottom surface of the heart monitor. In another example, the first surface 304 may contact the second surface 306. Button 316 may be positioned in housing 306 between electrodes 308 and 310.

Figure 4A:
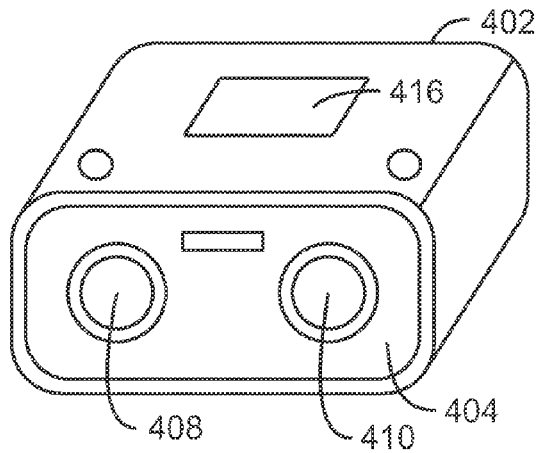
FIG. 4a is an illustration of a top perspective view of a heart monitor in accordance with an embodiment.
Figure 4B:
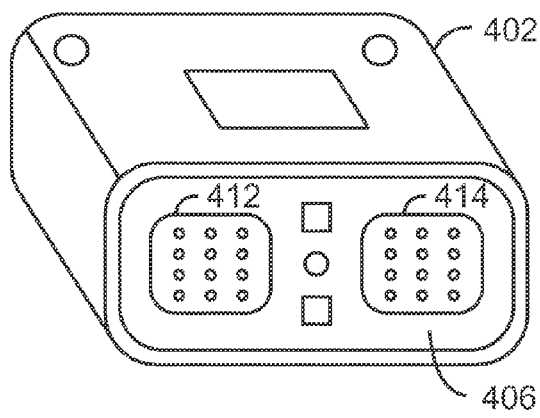
FIG. 4b is an illustration of a bottom perspective view of a heart monitor in accordance with an embodiment.
Figure 4C:
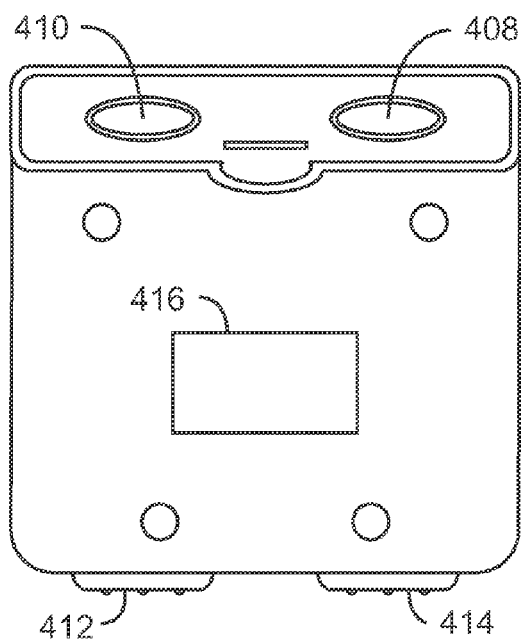
FIG. 4c is an illustration of a side perspective view of a heart monitor in accordance with an embodiment.

FIGS. 4a-4c are illustrations of top, bottom, and side perspective views of a heart monitor 400 in accordance with an embodiment. Disposed on a first surface 404 of a housing 402 are first electrode 408 and second electrode 410. Disposed on a second surface 406 of a housing 402 are a third electrode 412 and a fourth electrode 414. A button 416 is disposed on a surface of the housing 402.

All of the electrodes are made of a suitable conducting material. For example, the electrodes may be made of a metal. The electrodes may be of any geometrical shape. For example, the electrodes may be substantially circular, oval, or rectangular. The surface of the electrodes may be smooth, as illustrated by electrodes 408 and 410 in FIG. 4a, or textured, as illustrated by electrodes 412 and 414 in FIG. 4b. In an example, all of the electrodes may have a smooth surface. In another example, all of the electrodes may have a textured surface. In a further example, a portion of the electrodes may have a smooth surface and another portion of the electrodes may have a textured surface, as illustrated in FIG. 4c. The electrodes may have a flat surface or a curved surface. The curved surface may be concave or convex. In an example, all of the electrodes may have a flat surface. In another example, all of the electrodes may have a curved surface. In yet another example, a portion of the electrodes may have a flat surface and another portion of the electrodes may have a curved surface. The hand-held heart monitor may measure any suitable number of ECG leads, including, for example, twelve ECG leads. In another example, the electrodes may be capacitive in nature which may enable measuring bio-potentials from a distance, such as from over clothing, without requiring electrical contact to user's skin surface.

To measure ECG leads, a hand-held heart monitor may be placed against a user's unclothed torso in a series of four positions. If capacitive electrodes are used, ECG leads can be measured over clothing, without requiring electrical contact to a user's skin surface. In each position, a user's hands may each contact an electrode disposed on a first surface of a heart monitor. A user's entire hand may contact an electrode, one finger of a user's hand may contact an electrode, at least one finger of a user's hand may contact an electrode, or all of a user's fingers may contact an electrode. In each position, each electrode disposed on a second surface of a heart monitor may contact a different electrode position on a user's torso. The heart monitor may be held in each position for any suitable length of time, depending on the amount of data to be collected. For example, the heart monitor may be held in position for three seconds, ten seconds, thirty seconds, or more. The heart monitor may record each set of measured data in a memory after each position. Examples of each position are illustrated by FIGS. 6a, 7a, 8a, and 9a.

Figure 5:
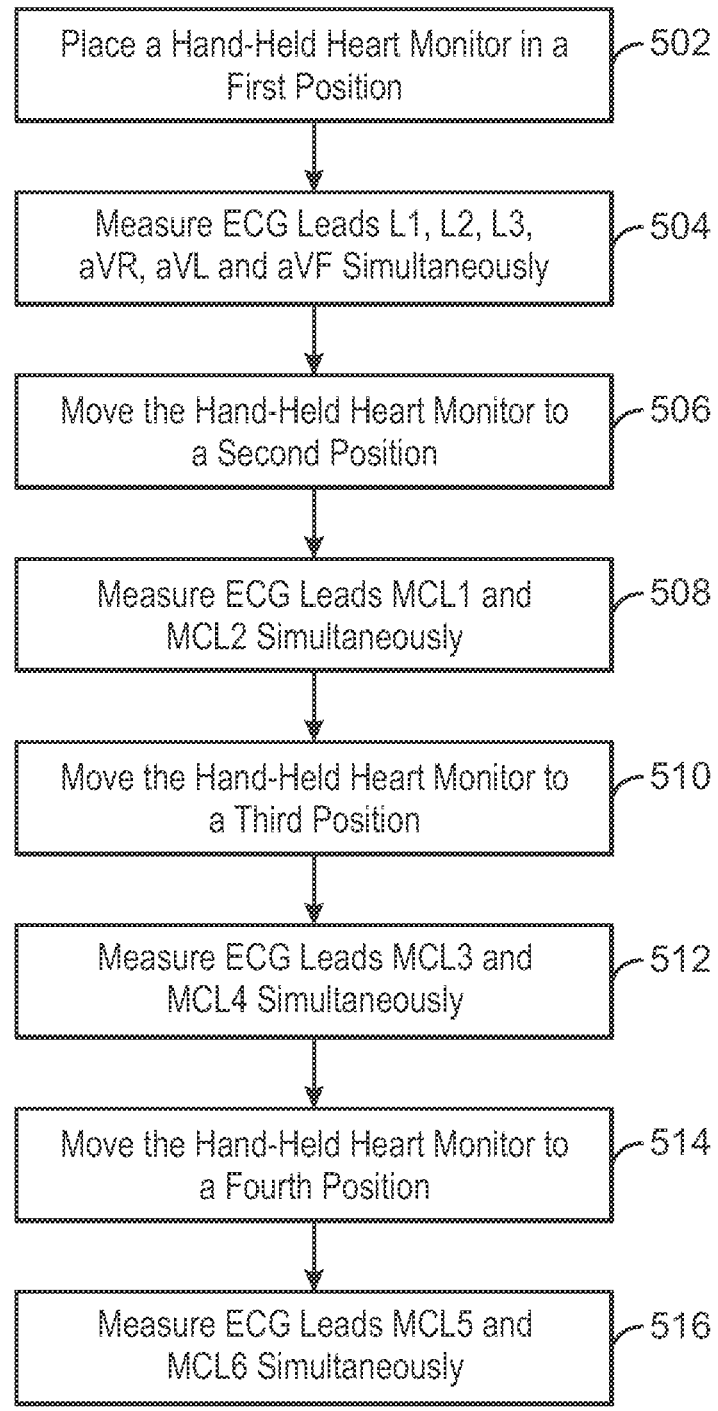
FIG. 5 is a flowchart illustrating a method of measuring twelve ECG leads.

FIG. 5 is a flowchart illustrating a method of measuring twelve ECG leads. As illustrated in FIG. 5, when placed against a user's torso, the hand-held heart monitor may measure 12 ECG leads in four steps 502, 506, 510, and 514. In order to measure 12 ECG leads in four steps, a hand-held heart monitor may measure at least two leads simultaneously in each step. For example, the heart monitor may measure 6 leads simultaneously. At block 502, a hand-held heart monitor may be placed in a first position against a user's torso or a user's left leg. At block 504, a hand-held heart monitor may measure ECG leads L1, L2, L3, aVR, aVL, and aVF simultaneously. At block 506, the hand-held heart monitor may be moved to a second position against a user's torso. At block 508, the hand-held heart monitor may measure ECG leads MCL1 and MCL2 simultaneously. At block 510, the hand-held heart monitor may be moved to a third position against a user's torso. At block 512, the hand-held heart monitor may measure ECG leads MCL3 and MCL4 simultaneously. AT block 514, the hand-held heart monitor may be moved to a fourth position against a user's torso. At block 516, the hand-held heart monitor may measure ECG leads MCL5 and MCL6 simultaneously. The data measured in each step may be recorded before moving to the next measurement step.

Figure 6A:
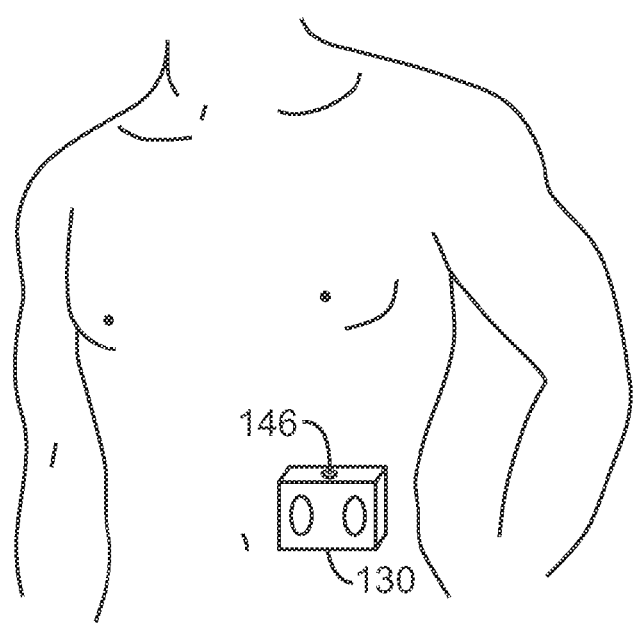
FIG. 6a is an illustration of a position of a heart monitor during measuring step 1 in accordance with an embodiment.
Figure 6B:
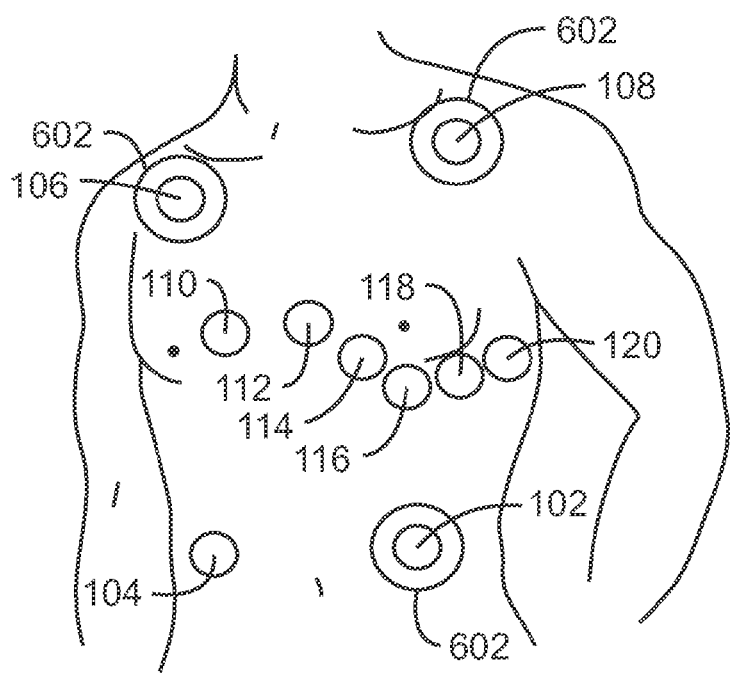
FIG. 6b is an illustration of the electrode positions measured by a heart monitor during measuring step 1 in accordance with an embodiment.

FIG. 6a is an illustration of a position of a heart monitor during measuring step 1 in accordance with an embodiment. The first position 600 may involve placing a user's left hand in contact with a first hand electrode (TL), disposed on a first surface of a hand-held heart monitor 130, placing a user's right hand in contact with a second hand electrode (TR), disposed on a first surface of a heart monitor 130, and placing one of a first (BL) and second (BR) electrode, disposed on a second surface of a heart monitor 130, against a user's lower left torso (i.e. at the left leg electrode position in a conventional 12-Lead ECG), as illustrated in FIG. 6a. Alternatively, one of a first (BL) and second (BR) electrodes can be placed anywhere on the left leg of a user including the thigh, ankle, knee, calf or foot. FIG. 6b is an illustration of the electrode positions 602 measured by a heart monitor 130 during measuring step 1 in accordance with an embodiment. When the hand-held heart monitor 130 is placed in the first position 600, electrode TL electrically contacts the left arm (LA) electrode position 108, electrode TR electrically contacts the right arm (RA) electrode position 106, and electrode BL electrically contacts the left leg (LL) electrode position 102, as illustrated in FIG. 6b.

By simultaneously contacting electrode positions RA, LA, and LL, ECG leads L1, L2, L3, aVR, aVL, and aVF can be simultaneously recorded. Amplifier channel, such as CH1, may be connected to electrodes BL and TL and amplifier channel CH2, may be connected to electrodes BL and TR.

Figure 7A:
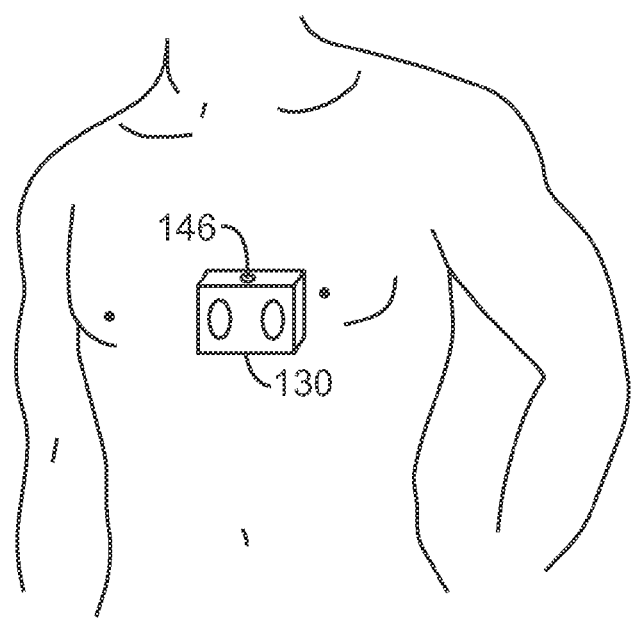
FIG. 7a is an illustration of a position of a heart monitor during measuring step 2 in accordance with an embodiment.
Figure 7B:
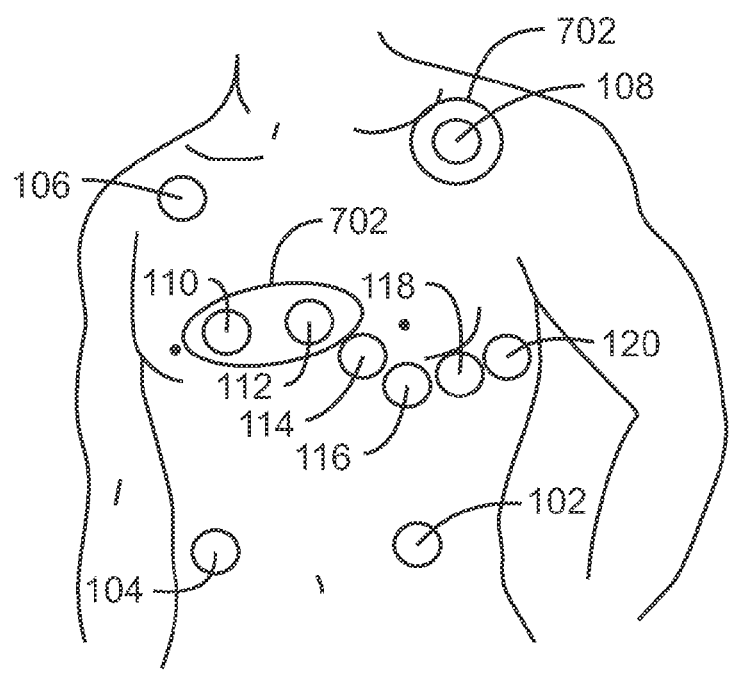
FIG. 7b is an illustration of the electrode positions measured by a heart monitor during measuring step 2 in accordance with an embodiment.

FIG. 7a is an illustration of a position of a heart monitor during measuring step 2 in accordance with an embodiment. The second position 700 may involve placing a user's left hand in contact with electrode TL, placing a user's right hand in contact with electrode TR, and placing electrodes BL and BR against a user's upper center torso, as illustrated in FIG. 7a. FIG. 7b is an illustration of the electrode positions 702 measured by a heart monitor 130 during measuring step 2 in accordance with an embodiment. When a hand-held heart monitor 130 is placed in the second position 700, electrode TL electrically contacts the LA electrode position 108, electrode BL electrically contacts the V2 chest electrode position 112, and electrode BR electrically contacts the V1 chest electrode position 110, as illustrated in FIG. 7b.

When the hand-held heart monitor 130 is placed in the second position 700, electrodes BR and TL may be connected to positive and negative inputs of an amplifier channel, such as amplifier channel CH3. Another amplifier channel, such as CH1, may be connected to electrodes BL and TL. ECG leads MCL1 and MCL2 are thus simultaneously measured.

Figure 8A:
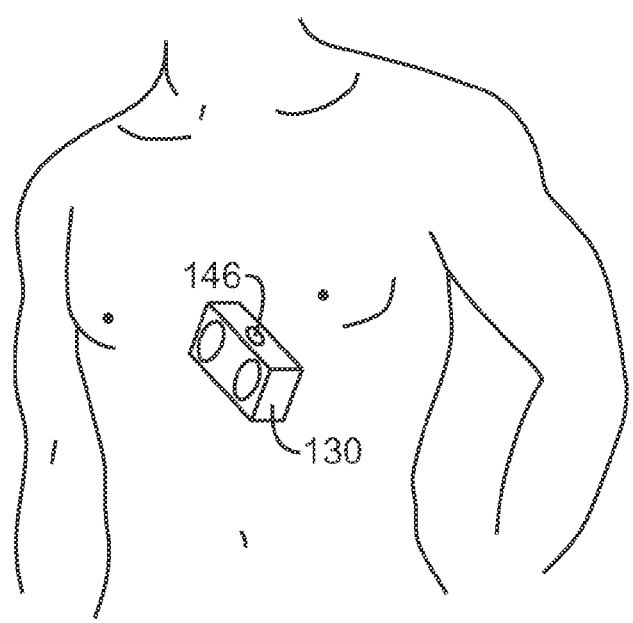
FIG. 8a is an illustration of a position of a heart monitor during measuring step 3 in accordance with an embodiment.
Figure 8B:
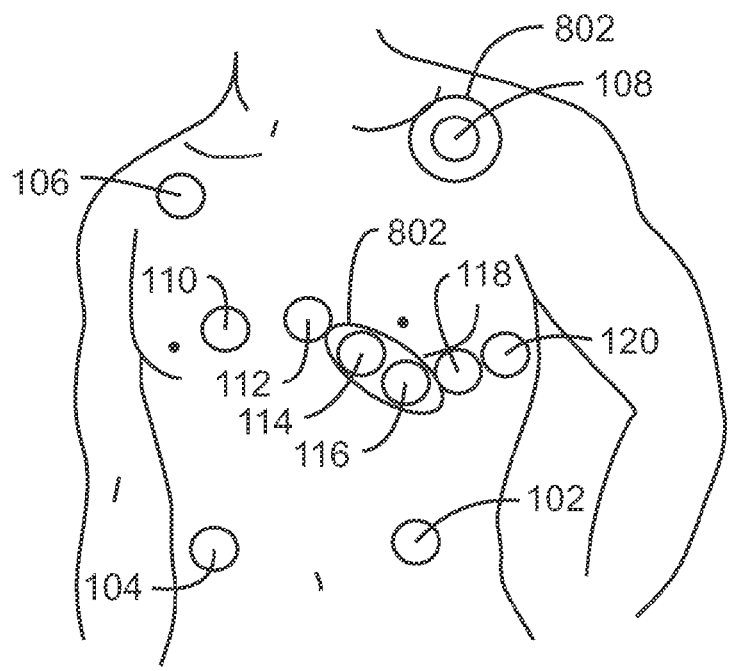
FIG. 8b is an illustration of the electrode positions measured by a heart monitor during measuring step 3 in accordance with an embodiment.

FIG. 8a is an illustration of a position of a heart monitor during measuring step 3 in accordance with an embodiment. The third position 800 may involve placing a user's left hand in contact with electrode TL, placing a user's right hand in contact with electrode TR, and placing electrodes BL and BR against a user's upper left torso, as illustrated in FIG. 8a. FIG. 8b is an illustration of the electrode positions 802 measured by a heart monitor 130 during measuring step 3 in accordance with an embodiment. When a hand-held heart monitor 130 is placed in the third position 800, electrode TL electrically contacts the LA electrode position 108, electrode BL electrically contacts the V4 chest electrode position 116, and electrode BR electrically contacts the V3 chest electrode position 114, as illustrated by FIG. 8b.

When the hand-held heart monitor 130 is placed in the third position 800, electrodes BR and TL may be connected to positive and negative inputs of an amplifier channel, such as amplifier channel CH3. Another amplifier channel, such as CH1, may be connected to electrodes BL and TL. ECG leads MCL3 and MCL4 are thus simultaneously measured.

Figure 9A:
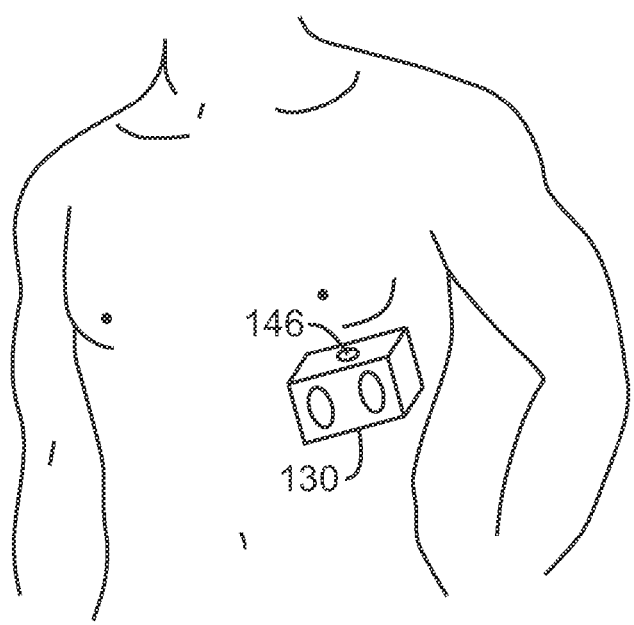
FIG. 9a is an illustration of a position of a heart monitor during measuring step 4 in accordance with an embodiment.
Figure 9B:
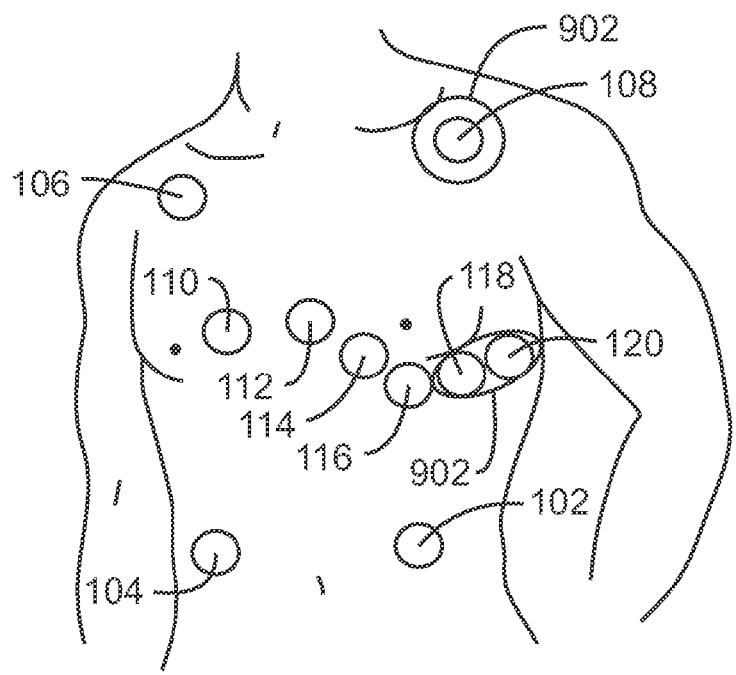
FIG. 9b is an illustration of the electrode positions measured by a heart monitor during measuring step 4 in accordance with an embodiment.

FIG. 9a is an illustration of a position of a heart monitor during measuring step 4 in accordance with an embodiment. The fourth position 900 may involve placing a user's left hand in contact with electrode TL, placing a user's right hand in contact with electrode TR, and placing electrodes BL and BR against the upper left side of a user's torso, as illustrated in FIG. 9a. FIG. 9b is an illustration of the electrode positions 902 measured by a heart monitor 130 during measuring step 4 in accordance with an embodiment. When a hand-held heart monitor 130 is placed in the fourth position 900, electrode TL electrically contacts the LA electrode position 108, electrode BL electrically contacts the V6 chest electrode position 120, and electrode BR electrically contacts the V5 chest electrode position 118, as illustrated in FIG. 9b.

When the hand-held heart monitor 130 is placed in the fourth position 900, electrodes BR and TL may be connected to positive and negative inputs of an amplifier channel, such as CH3. Another amplifier channel, such as CH1, may be connected to electrodes BL and TL. ECG leads MCL5 and MCL6 are thus simultaneously measured.

After each measurement step, a button 146 located on the hand-held heart monitor 130 may be pressed to indicate to the device to advance to the next measurement step. Pressing the button 146 may further indicate to the hand-held heart monitor 130 to store the ECG data measured in each step in a memory. The memory may be internal to the hand-held heart monitor 130. In another example, commands may be wirelessly sent by a phone or computing device to the hand-held heart monitor to indicate to the heart monitor to advance to the next step, in which case, button 146 may be eliminated.

After completing the four measurement steps, the hand-held heart monitor may transmit the measured ECG data to another location. The other location may be a type of storage device. For example, the hand-held heart monitor may transmit the ECG data to a back-end server, such as a server belonging to a patient's health care provider. In another example, the data may be transmitted to a health care provider's email.

The hand-held monitor may transmit the data through a variety of methods. For example, the hand-held heart monitor may transmit the data over an internet connection, such as a wired internet connection, a LAN connection, or a WAN internet connection. In another example, the data may be transmitted over a telephone connection, such as a landline telephone connection or a wireless telephone connection. In another example, data may be transmitted by the heart monitor using wireless communication technology such as Bluetooth, Zigbee, or WiFi to another device such as a mobile phone or a computing device such as a tablet PC or laptop. In a further example, the data may be transmitted over a fax line.

The hand-held heart monitor may automatically transmit the measured ECG data to another device. In an example, the heart monitor may automatically transmit the data to another device upon completion of measuring all ECG leads. In another example, the heart monitor may automatically transmit the ECG data to another device after each measurement step. The heart monitor may transmit data to another device in response to a signal from the user. In an example, the heart monitor may transmit data to another device in response to a user pressing a button. For example, the heart monitor may transmit data to another device when a button is pressed after each measurement step. In another example, the heart monitor may transmit data to another device when a button is pressed after all ECG leads have been measured. In another example, a heart monitor may transfer data to another device when a connection, such as an internet connection or a telephone connection, is established between the heart monitor and another device.

The hand-held heart monitor may display the measured ECG data to the user on a display disposed on the hand-held heart monitor. In an example, the hand-held heart monitor may display the measured ECG data to the user and transmit the data to another device. In another example, the hand-held heart monitor may only display the measured ECG data to the user.

It will be understood by a person skilled in the art that a user may be a patient and may use a hand-held heart monitor as currently described to self-measure his or her ECG leads. It will also be understood that a health care provider may use a hand-held heart monitor as currently described to measure a patient's ECG leads. In such a case, a patient's hands would contact the TL and TR electrodes.

Figure 10A:
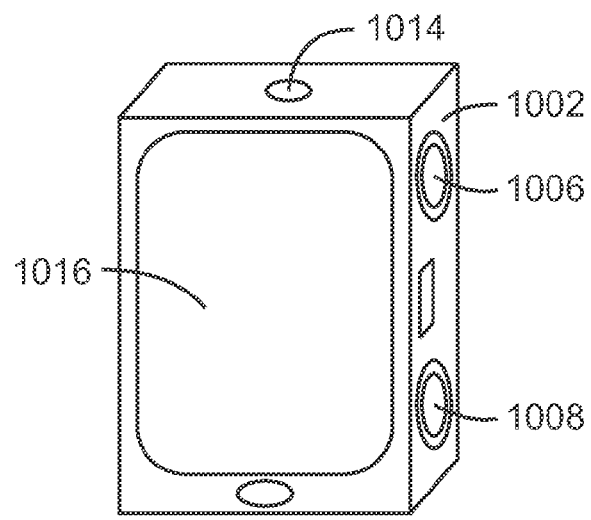
FIG. 10a is an illustration of a right side perspective view of a portable phone in accordance with an embodiment.
Figure 10B:
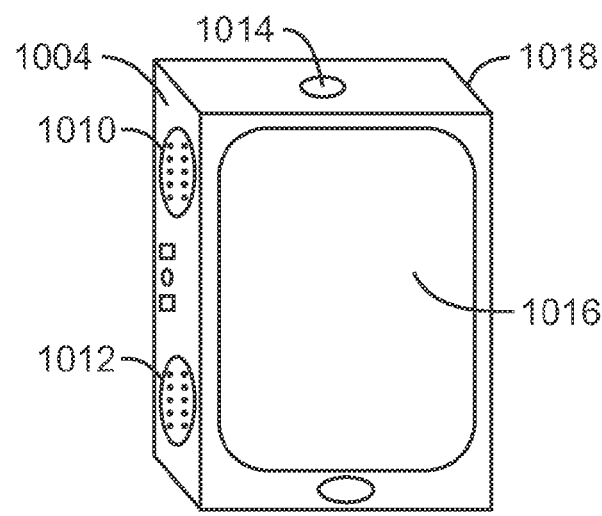
FIG. 10b is an illustration of a left side perspective view of a portable phone in accordance with an embodiment.

FIGS. 10a-10b are illustrations of left and right side perspective views of a portable phone in accordance with an embodiment. A hand-held heart monitor 130 may be incorporated in a portable phone to form a health phone 1000. In an example, the portable phone may be a cellular phone, such as a feature phone or a smartphone. The hand-held heart monitor may include at least three electrodes or at least four electrodes disposed on at least one surface of the health phone 1000. In an example, electrode 1006 and electrode 1008 may be disposed on a first surface 1002 of health phone, such as a side of the health phone 1000. Electrode 1010 and electrode 1012 may be disposed on a second surface 1004 of health phone 1000, such as the side directly opposite and parallel to the first side 1002 of the health phone 1000.

A portable phone with a hand-held heart monitor incorporated therein, otherwise known as a health phone 1000, may also include a memory, such as a flash memory, a processor, and an operating system. The health phone 1000 may also include an application designed to operate an incorporated heart monitor. The application may have a button used to activate the heart monitor and to indicate when to move on to the next measurement step. The health phone 1000 may also have at least one external button 1014 mounted on the housing 1018 of the health phone 1000 to operate an incorporated heart monitor. The health phone 1000 may further have a display 1016 capable of visually displaying measured ECG data to a user, such as a patient.

Using an incorporated hand-held heart monitor, the health phone may measure 12 ECG leads. In particular, a health phone may measure aVR, aVF, aVL, MCL1, MCL2, MCL3, MCL4, MCL5, MCL6, L1, L2, and L3 ECG leads. The health phone may measure 6 ECG leads simultaneously. In particular, the health phone may measure L1, L2, L3, aVR, aVL, and aVF ECG leads simultaneously. Furthermore, the health phone may measure MCL1 and MCL2 ECG leads simultaneously, MCL3 and MCL4 ECG leads simultaneously, and MCL5 and MCL6 ECG leads simultaneously. Therefore, the health phone with four electrodes may measure 12 ECG leads in four measurement steps.

A health phone may be used in the method described above regarding a hand-held heart monitor to measure 12 ECG leads. In particular, the health phone may be placed against a user's torso in the first, second, third, and fourth positions described above. In another embodiment, the health phone may be placed against the user's left leg in the first position and against the user's torso in the second, third, and fourth positions described above. In each position, a user's hands may contact the electrodes on a first surface and a user's torso may contact at least one electrode on a second surface. At each position, at least two ECG leads may be measured, in the method described above.

The disclosure set forth above may encompass multiple distinct embodiments with independent utility. The specific embodiments disclosed and illustrated herein are not to be considered in a limiting sense, because numerous variations are possible. The subject matter of this disclosure includes all novel and nonobvious combination and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether directed to a different embodiment or to the same embodiment, and whether broader, narrower, equal, or different in scope to the original claims, also are regarded as included within the subject matter of the present disclosure.

Where the claims recite "a" or "a first" element or the equivalent thereof, such claims include one or more such elements, neither requiring nor excluding two or more such elements. Further, ordinal indicators, such as first, second, or third, for identified elements are used to distinguish between the elements, and do not indicate a required or limited number of such elements, and do not indicate a particular position or order of such elements unless otherwise specifically stated.

What is claimed is:

1. A heart monitor comprising:
   a housing;
   first and second electrodes disposed on a first surface of the housing, the first electrode to be in contact with a user's left hand, the second electrode to be in contact with the user's right hand;
   third and fourth electrodes disposed on a second surface of the housing, the third and fourth electrodes to be held by the user against the user's body while the user contacts the first and second electrodes with the user's left and right hands; and
   a processor to record lead measurements corresponding to voltage differences between the first, second, third, and fourth electrodes;
   wherein the third and fourth electrodes are to be held against adjacent standard chest electrode positions and the processor simultaneously records the lead measurements corresponding to the adjacent standard chest electrode positions during a single positioning of the heart monitor.

2. The heart monitor of claim 1, wherein the processor records measurements for twelve ECG leads.

3. The heart monitor of claim 2, wherein the processor records the measurements for the twelve ECG leads in four positionings of the heart monitor.

4. The heart monitor of claim 1, wherein the processor records at least three standard ECG leads simultaneously in each measurement step.

5. The heart monitor of claim 1, wherein the processor records measurements for ECG leads L1, L2, L3, aVR, aVL, aVF, MCL1, MCL2, MCL3, MCL4, MCL5, and MCL6.

* * * * *